United States Patent [19]

Child et al.

[11] Patent Number: 5,012,033

[45] Date of Patent: Apr. 30, 1991

[54] ISOPARAFFIN-OLEFIN ALKYLATION PROCESS AND CATALYST COMPOSITION THEREOF

[75] Inventors: Jonathan E. Child, Sewell, N.J.; Albin Huss, Jr., Chadds Ford; Clinton R. Kennedy, West Chester, both of Pa.; David O. Marler, Deptford, N.J.; Samuel A. Tabak, Wenonah, N.J.

[73] Assignee: Mobil Oil Corp., Fairfax, Va.

[21] Appl. No.: 470,016

[22] Filed: Jan. 25, 1990

Related U.S. Application Data

[63] Continuation-in-part of Ser. No. 254,524, Oct. 6, 1988, Pat. No. 4,954,325, and a continuation-in-part of Ser. No. 98,176, Sep. 18, 1987, abandoned, which is a continuation-in-part of Ser. No. 890,268, Jul. 29, 1986, abandoned.

[51] Int. Cl.$^5$ ............................ C07C 2/58; C07C 2/60
[52] U.S. Cl. .................... 585/722; 585/726; 585/727
[58] Field of Search ................ 585/722, 726, 727

[56] References Cited

U.S. PATENT DOCUMENTS

| | | | |
|---|---|---|---|
| 2,363,116 | 11/1944 | Bruner | 585/725 |
| 2,843,642 | 7/1958 | Kelly | 585/726 |
| 2,939,890 | 6/1960 | Hervert et al. | 585/463 |
| 3,131,230 | 4/1964 | Hervert et al. | 585/463 |
| 3,251,902 | 5/1966 | Garwood et al. | 585/722 |
| 3,450,644 | 6/1969 | Lanewala et al. | 502/38 |
| 3,541,180 | 11/1970 | Thomas | 585/722 |
| 3,549,557 | 12/1970 | Bolton et al. | 502/73 |
| 3,624,173 | 11/1971 | Kirsch et al. | 585/467 |
| 3,644,565 | 2/1972 | Biale | 585/722 |
| 3,647,916 | 3/1972 | Caesar et al. | 585/722 |
| 3,655,813 | 4/1972 | Kirsch et al. | 585/722 |
| 3,706,814 | 12/1972 | Kirsch et al. | 585/722 |
| 3,738,977 | 6/1973 | Biale | 526/108 |
| 3,840,613 | 10/1974 | Eberly, Jr. et al. | 585/722 |
| 3,855,342 | 12/1974 | Huang et al. | 585/726 |
| 3,862,258 | 1/1975 | Huang et al. | 585/726 |
| 3,893,942 | 7/1975 | Yang | 585/906 |
| 3,906,054 | 9/1975 | Faeding et al. | 585/722 |
| 3,917,738 | 11/1975 | Fenske et al. | 585/722 |
| 4,377,721 | 3/1983 | Chester et al. | 585/331 |
| 4,384,161 | 5/1983 | Huang | 585/726 |
| 4,439,409 | 3/1984 | Puppe et al. | 423/328 |
| 4,665,265 | 5/1987 | Chu et al. | 585/722 |
| 4,826,667 | 5/1989 | Zones et al. | 423/277 |
| 4,918,255 | 4/1990 | Chou et al. | 585/726 |

FOREIGN PATENT DOCUMENTS

| | | | |
|---|---|---|---|
| 0231860 | 8/1987 | European Pat. Off. | 502/64 |
| 0293032 | 11/1988 | European Pat. Off. | 502/64 |

*Primary Examiner*—Anthony McFarlane
*Attorney, Agent, or Firm*—Alexander J. McKillop; Charles J. Speciale; Dennis P. Santini

[57] ABSTRACT

Isoparaffin-olefin alkylation is carried out in the presence of a Lewis acid-promoted catalyst, said catalyst comprising a synthetic porous crystalline material characterized in its calcined form by an X-ray diffraction pattern including interplanar d-spacings at 12.36±0.4, 11.03±0.2, 8.83±0.14, 6.18±0.12, 6.00±0.10, 4.06±0.07, 3.91±0.07 and 3.42±0.06 Angstroms.

24 Claims, 1 Drawing Sheet

ISOPARAFFIN-OLEFIN ALKYLATION PROCESS AND CATALYST COMPOSITION THEREOF

CROSS-REFERENCE TO RELATED APPLICATIONS

This application is a continuation-in-part of U.S. patent application Ser. No. 254,524, filed Oct. 6, 1988, which is now U.S. Pat. No. 9,954,325, and is a continuation-in-part of U.S. patent application Ser. No. 98,176, filed Sept. 18, 1987, now abandoned which is a continuation-in-part of U.S. patent application Ser. No. 890,268, filed Jul. 29, 1986, now abandoned.

BACKGROUND OF THE INVENTION

The present invention relates to an isoparaffin-olefin alkylation process employing, as catalyst, a Lewis acid-promoted zeolite of a particular type to provide an alkylate product useful, inter alia, as an octane enhancer for gasoline.

As a result of the curtailment in the use of tetraethyl lead as an octane-improving additive for gasoline, not only has the production of unleaded gasoline increased but the octane number specification of all grades of gasoline have increased as well. Isoparaffin-olefin alkylation is a key route to the production of highly branched paraffin octane enhancers which are to be blended into gasolines.

Alkylation involves the addition of an alkyl group to an organic molecule. Thus, an isoparaffin can be reacted with an olefin to provide an isoparaffin of higher molecular weight. Industrially, alkylation often involves the reaction of $C_2$-$C_5$ olefins with isobutane in the presence of an acidic catalyst. Alkylates are valuable blending components for the manufacture of premium gasolines due to their high octane ratings.

In the past, alkylation processes have included the use of hydrofluoric acid or sulfuric acid as catalysts under controlled temperature conditions. Low temperatures are utilized in the sulfuric acid process to minimize the undesirable side reaction of olefin polymerization and the acid strength is generally maintained at 88-94 percent by the continuous addition of fresh acid and the continuous withdrawal of spend acid. The hydrofluoric acid process is less temperature-sensitive and the acid is easily recovered and purified.

The typical types of alkylation currently used to produce high octane gasoline blending component, that is, the hydrofluoric acid and sulfuric acid alkylation processes, have inherent drawbacks including environmental concerns, acid consumption and disposal of corrosive materials. With the increasing demands for octane and the increasing environmental concerns, it has been desirable to develop an alkylation process based on a solid catalyst system. The catalyst of the present invention offers a refiner a more environmentally acceptable and more selective alkylation process than the currently used hydro- fluoric and sulfuric acid alkylation processes.

The alkylation process of U.S. Pat. No. 3,862,258 utilizes a catalyst comprising a macroreticular acid cation exchange resin and boron trifluoride. It is reported in this patent that the life of such a catalyst can be extended by the presence in the reaction mixture of closely controlled amounts of water which can be added to the feed as water or as a water-producing compound, for example, in the form of an alcohol such as methanol.

U.S. Pat. No. 3,855,342 also discloses the use of a combination of a macroreticular acid cation exchange resin and boron trifluoride as an isoparaffin-olefin alkylation catalyst. The boron trifluoride component is present in an amount sufficient to saturate the cation exchange resin component of the catalyst system.

Crystalline metallosilicates, or zeolites, have also been widely investigated for use in the catalysis of isoparaffin alkylation. For example, U.S. Pat. No. 3,251,902 describes the use of a fixed bed of ion-exchanged crystalline aluminosilicate having a reduced number of available acid sites for the liquid phase alkylation of $C_4$-$C_{20}$ branched-chain paraffins with $C_2$-$C_{12}$ olefins. The patent further discloses that the $C_4$-$C_{20}$ branched-chain paraffin should be allowed to substantially saturate the crystalline aluminosilicate before the olefin is introduced to the alkylation reactor.

U.S. Pat. No. 3,450,644 discloses a method for regenerating a zeolite catalyst used in hydrocarbon conversion processes involving carbonium ion intermediates.

U.S. Pat. No. 3,549,557 describes the alkylation of isobutane with $C_2$-$C_3$ olefins using certain crystalline aluminosilicate zeolite catalysts in a fixed, moving or fluidized bed system, the olefin being preferably injected at various points in the reactor.

U.S. Pat. No. 3,644,565 discloses the alkylation of a paraffin with an olefin in the presence of a catalyst comprising a Group VIII noble metal present on a crystalline aluminosilicate zeolite, the catalyst having been pretreated with hydrogen to promote selectivity.

U.S. Pat. No. 3,647,916 describes an isoparaffin-olefin alkylation process featuring the use of an ion-exchanged crystalline aluminosilicate, isoparaffin/olefin mole ratios below 3:1 and regeneration of the catalyst.

U.S. Pat. No. 3,655,813 discloses a process for alkylating $C_4$-$C_5$ isoparaffins with $C_3$-$C_9$ olefins using a crystalline aluminosilicate zeolite catalyst wherein a halide adjuvant is employed in the alkylation reactor. The isoparaffin and olefin are introduced into the alkylation reactor at specified concentrations and catalyst is continuously regenerated outside the alkylation reactor.

U.S. Pat. No. 3,893,942 describes an isoparaffin alkylation process employing, as catalyst, a Group VIII metal-containing zeolite which is periodically hydrogenated with hydrogen in the gas phase to reactivate the catalyst when it has become partially deactivated.

U.S. Pat. No. 3,236,671 discloses the use, in alkylation, of crystalline aluminosilicate zeolites having silica to alumina mole ratios above 3 and also discloses the use of various metals exchanged and/or impregnated on such zeolites.

U.S. Pat. No. 3,706,814 discloses another zeolite-catalyzed isoparaffin-olefin alkylation process and further provides for the addition of $C_5+$ paraffins such as Udex raffinate or $C_5+$ olefins to the alkylation reactor feed and the use of specific reactant proportions, halide adjuvants, etc.

U.S. Pat. No. 3,624,173 discloses the use, in isoparaffin-olefin alkylation, of zeolite catalysts containing gadolinium.

U.S. Pat. No. 3,738,977 discloses alkylation of paraffins with ethylene employing a zeolite catalyst which possesses a Group VIII metal component, the catalyst having been pretreated with hydrogen.

U.S. Pat. No. 3,917,738 describes a process for alkylating an isoparaffin with an olefin using a solid, particulate catalyst capable of absorbing the olefin. The isoparaffin and the olefin are admixed to form a reactant stream in contact with catalyst particles at the upstream end of an adsorption zone after which the reactants are passed concurrently with the catalyst so that a controlled amount of olefin is adsorbed onto the catalyst before the combination of reactants and catalyst is introduced into an alkylation zone. This controlled olefin adsorption is said to prevent polymerization of the olefin during alkylation.

U.S. Pat. No. 4,384,161 describes a process of alkylating isoparaffins with olefins to provide alkylate employing as catalyst a large pore zeolite capable of absorbing 2,2,4-trimethylpentane, e.g., ZSM-4, ZSM-20, ZSM-3, ZSM-18, zeolite Beta, faujasite, mordenite, zeolite Y and the rare earth metal-containing forms thereof, and a Lewis acid such as boron trifluoride, antimony pentafluoride or aluminum trichloride. The use of a large pore zeolite in combination with a Lewis acid in accordance with this patent is reported to greatly increase the activity and selectivity of the zeolite thereby effecting alkylation with high olefin space velocity and low isoparaffin/olefin ratio.

SUMMARY OF THE INVENTION

In accordance with the present invention, isoparaffin-olefin alkylation is catalyzed by a Lewis acid-promoted zeolite, wherein the zeolite is characterized by an X-ray diffraction pattern including interplanar d-spacings at 12.36±0.4, 11.03±0.2, 8.83±0.14, 6.18±0.12, 6.00±0.10, 4.06±0.07, 3.91±0.07 and 3.42±0.06 Angstroms.

Isoparaffin-light olefin alkylation plays an important role in the manufacture of high octane gasoline blending stocks with alkylate typically comprising 10–15% of the gasoline pool. Alkylate is an especially valuable component of the gasoline pool as it possesses both high research and motor octane (low sensitivity) numbers, contains no olefins or aromatics and little or no sulfur, demonstrates excellent stability and is clean burning. One measure of the selectivity of an alkylation catalyst is the $C_{9+}$ yield. This fraction generally results from oligomerization of the feed olefins resulting in a loss of alkylate yield, reduced alkylate quality and the possible formation of an acidic sludge fraction. The alkylation catalyst composition employed in the present process provides reduced $C_{9+}$ yields relative to such known zeolite alkylation catalysts as zeolite HY, e.g. as disclosed in U.S. Pat. No. 3,865,984, as well as such known catalyst systems as $BF_3$-promoted zeolite Beta and the even older hydrofluoric acid and sulfuric acid type alkylation catalysts.

The alkylate produced by the process of this invention is of high quality based on both research and motor octane numbers and as such is particularly well suited for blending into the gasoline pool.

DESCRIPTION OF SPECIFIC EMBODIMENTS

Figure 1:
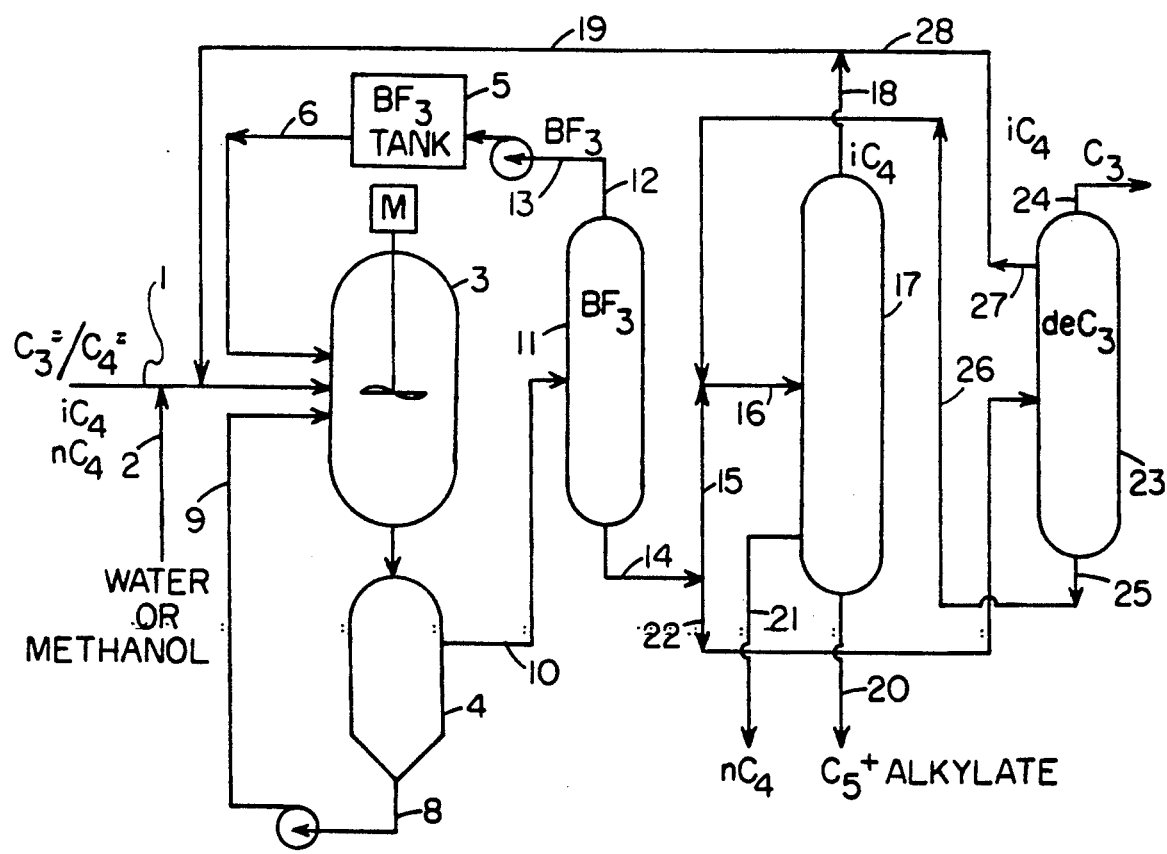
FIG. 1 represents a block flow diagram of an embodiment of the alkylation process of the present invention.

The entire contents of applications Ser. Nos. 254,524; 98,176, and 890,268 are incorporated herein by reference.

As previously stated, the heterogeneous alkylation catalyst compositions employed in the alkylation process of this invention comprises a Lewis acid promoter and a synthetic porous crystalline material, or zeolite. A Lewis acid is generally considered to be a molecule which is capable of combining with another molecule or ion by forming a covalent chemical bond with two electrons from the second molecule or ion, which is to say, a Lewis acid is an electron acceptor. Examples of Lewis acids include boron trifluoride ($BF_3$), antimony pentafluoride ($SbF_5$) and aluminum chloride ($AlCl_3$). The present invention contemplates the use of these and all other Lewis acids including those disclosed in "Friedel-Crafts and Related Reactions", Interscience Publishers, Chapters III and IV (1963), the contents of which are incorporated by reference herein. $BF_3$ is a preferred Lewis acid for use in the alkylation process of this invention. In the case of $BF_3$, this promoter is preferably present in the alkylation zone in an amount which exceeds that required to saturate the zeolite catalyst component considered not only as the zeolite per se but as any other material, e.g., binder or matrix material, which might be associated therewith.

Usually, the excess $BF_3$ is present at from about 0.1 to about 25 wt % of hydrocarbon feed. Preferably, the excess $BF_3$ is present at from about 1 to 10 wt % of hydrocarbon feed. The amount of excess $BF_3$ required relates indirectly to the isobutane/olefin ratio such that when the isobutane/olefin ratio is 2/1, 5 wt % or more excess $BF_3$ is preferred. When the isobutane/olefin ratio is about 10/1, 1 wt % or more excess $BF_3$ is preferred.

In its calcined form, the synthetic porous crystalline material component employed in the catalyst composition used in the process of this invention is characterized by an X-ray diffraction pattern including the following lines:

TABLE A

| Interplanar d-Spacing (A) | Relative Intensity, $I/I_o \times 100$ |
| --- | --- |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

Alternatively, it may be characterized by an X-ray diffraction pattern in its calcined form including the following lines:

TABLE B

| Interplanar d-Spacing (A) | Relative Intensity, $I/I_o \times 100$ |
| --- | --- |
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |
| 3.42 ± 0.06 | VS |

More specifically, the calcined form may be characterized by an X-ray diffraction pattern including the following lines:

TABLE C

| Interplanar d-Spacing (A) | Relative Intensity, $I/I_o \times 100$ |
| --- | --- |
| 12.36 ± 0.4 | M-VS |
| 11.03 ± 0.2 | M-S |
| 8.83 ± 0.14 | M-VS |

TABLE C-continued

| Interplanar d-Spacing (A) | Relative Intensity, $I/I_o \times 100$ |
| --- | --- |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

Most specifically, it may be characterized in its calcined form by an X-ray diffraction pattern including the following lines:

TABLE D

| Interplanar d-Spacing (A) | Relative Intensity, $I/I_o \times 100$ |
| --- | --- |
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractomer. From these, the relative intensites, 100 $I/I_o$, where $I_o$ is the intensity of the strongest line or peak, and d (obs.) the interplanar spacing in Angstrom Units (A), corresponding to the recorded lines, were determined. In Tables A-D, the relative intensities are given in terms of the symbols W=weak, M=medium, S=strong, VS=very strong. In terms of intensities, these may be generally designated as follows:

| W = | 0-20 |
| M = | 20-40 |
| S = | 40-60 |
| VS = | 60-100 |

It should be understood that these X-ray diffraction patterns are characteristic of all species of the zeolite. The sodium form as well as other cationic forms reveal substantially the same pattern with some minor shifts in interplanar spacing and variation in relative intensity. Other minor variations can occur depending on the ratio of structural components, e.g. silicon to aluminum mole ratio of the particular sample, as well as its degree of thermal treatment.

Examples of such porous crystalline materials include the PSH-3 composition of U.S. Pat. No. 4,439,409, incorporated herein by reference, and MCM-22.

Zeolite MCM-22 has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

wherein R is an organic component. The Na and R components are associated with the zeolite as a result of their presence during crystallization, and are easily removed by post-crystallization methods hereinafter more particularly described.

Zeolite MCM-22 is thermally stable and exhibits a high surface area greater than about 400 m²/gm as measured by the BET (Bruenauer, Emmet and Teller) test and unusually large sorption capacity when compared to previously described crystal structures having similar X-ray diffraction patterns. As is evident from the above formula, MCM-22 is synthesized nearly free of Na cations and thus possesses acid catalysis activity as synthesized. It can, therefore, be used as a component of the alkylation catalyst composition herein without having to first undergo an exchange step. To the extent desired, however, the original sodium cations of the as-synthesized material can be replaced in accordance with techniques well known in the art, at least in part, by ion exchange with other cations. Preferred replacement cations include metal ions, hydrogen ions, hydrogen precursor, e.g., ammonium, ions and mixtures thereof. Particularly preferred cations are those which tailor the activity of the catalyst for alkylation. These include hydrogen, rare earth metals and metals of Groups IIA, IIIA, IVA, IB, IIB, IIIB, IVB and VIII of the Periodic Table of the Elements.

In its calcined form, zeolite MCM-22 appears to be made up of a single crystal phase with little or no detectable impurity crystal phases and has an X-ray diffraction pattern including the lines listed in above Tables A-D.

Prior to its use in the alkylation catalyst composition herein, the synthetic porous crystalline material zeolite should be subjected to thermal treatment to remove part or all of any organic constituent present therein.

The zeolite present in the alkylation catalyst composition herein can also be used in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be associated chemically and/or physically with the zeolite and/or matrix with which the zeolite may be optionally composited. Thus, e.g., the hydrogenating component can be introduced into the catalyst composition by way of co-crystallization, exchanged into the composition to the extent a Group IIIA element, e.g., aluminum, is in the structure, impregnated therein or intimately physically admixed therewith. Such component can be impregnated in, or on, the zeolite such as, for example, by, in the case of platinum, treating the zeolite with a solution containing the platinum metal-containing ion. Thus, suitable platinum compounds for this purpose include chloroplatinic acid, platinous chloride and various compounds containing the platinum amine complex.

The zeolite, especially in its metal, hydrogen and ammonium forms, can be beneficially converted to another form by thermal treatment. This thermal treatment is generally performed by heating one of these forms at a temperature of at least about 370° C. for at least 1 minute and generally not longer than 20 hours. While subatmospheric pressure can be employed for the thermal treatment, atmospheric pressure is preferred simply for reasons of convenience. The thermal treatment can be performed at a temperature of up to about 925° C.

Prior to its use in the alkylation catalyst composition and process of this invention, the zeolite crystals should be at least partially dehydrated. This can be accomplished by heating the crystals to a temperature in the range of from about 200° C. to about 595° C. in an atmosphere such as air, nitrogen, etc., and at atmospheric, subatmospheric or superatmospheric pressures for a period of from between about 30 minutes to about 48 hours. Dehydration can also be performed at room temperature merely by placing the crystalline material in a vacuum but a longer time will be required to achieve a suitable degree of dehydration.

Zeolite MCM-22 can be prepared from a reaction mixture containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, said reaction mixture having a composition, in terms of mole ratios of oxides, within the following ranges:

| Reactants; | Useful | Preferred |
|---|---|---|
| $YO_2/X_2O_3$ | 10–60 | 10–40 |
| $H_2O/YO_2$ | 5–100 | 10–50 |
| $OH^-/YO_2$ | 0.01–1.0 | 0.1–0.5 |
| $M/YO_2$ | 0.01–2.0 | 0.1–1.0 |
| $R/YO_2$ | 0.05–1.0 | 0.1–0.5 |

In a preferred method of synthesizing zeolite MCM-22, the $YO_2$ reactant contains a substantial amount of solid $YO_2$, e.g., at least about 30 wt. % solid $YO_2$. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors MCM-22 crystal formation from the above mixture and is a distinct difference over the synthesis method disclosed in U.S. Pat. No. 4,439,409. If another source of oxide of silicon, e.g., Q-Brand (a sodium silicate comprised of about 28.8 wt. % of $SiO_2$, 8.9 wt. % $Na_2O$ and 62.3 wt. % $H_2O$) is used, crystallization may yield little if any MCM-22 crystalline material and impurity phases of other crystal structures, e.g., ZSM-12, may be produced. Preferably, therefore, the $YO_2$, e.g., silica, source contains at least about 30 wt. % solid $YO_2$, e.g., silica, and more preferably at least about 40 wt. % solid $YO_2$, e.g., silica.

Crystallization of the MCM-22 crystalline material can be carried out at either static or stirred conditions in a suitable reactor vessel such as, e.g., polypropylene jars or teflon-lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 material will vary with the nature of the reaction mixture employed and the crystallization conditions. In all cases, synthesis of the MCM-22 crystals is facilitated by the presence of at least about 0.01 percent, preferably about 0.10 percent and still more preferably about 1 percent, seed crystals based on the total weight of the crystalline product formed.

The zeolite crystals can be shaped into a wide variety of particle sizes. Generally speaking, the particles can be provided in the form of a powder, a granule or a molded product such as an extrudate having a particle size sufficient to pass through a 2 mesh (Tyler) screen and be substantially retained on a 400 mesh (Tyler) screen. In cases where the catalyst is molded, such as by extrusion, the crystals can be extruded before drying or partially dried and then extruded.

It may be desired to incorporate the zeolite crystalline material with another material, i.e., a binder, which is resistant to the temperatures and other conditions employed in the isoparaffin alkylation process of this invention. Suitable binder materials include active and inactive materials and synthetic or naturally occurring zeolites as well as inorganic materials such as clays, silica and/or metal oxides such as alumina. The latter can be either naturally occurring or provided in the form of gelationous precipitates or gels including mixtures of silica and metal oxides. Use of a binder material in conjunction with the zeolite, i.e., combined therewith or present during its synthesis, which itself is catalytically active may change the conversion and/or selectivity of the catalyst. Inactive materials suitably serve as diluents to control the amount of conversion so that isoparaffin alkylation products can be obtained economically and in a controlled fashion without having to employ other means for controlling the rate of reaction. These materials can be incorporated into naturally occurring clays, e.g., bentonite and kaolin, to improve the crush strength of the zeolite under commercial isoparaffin alkylation operating conditions. Good crush strength is an advantageous attribute for commercial use since it prevents or delays breaking down of the catalyst into powder-like materials.

Naturally occurring clays which can be composited with the zeolite crystals include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the zeolite also include inorganic oxides, notably alumina.

Apart from or in addition to the foregoing binder materials, the zeolite crystals can be composited with an inorganic oxide matrix such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia, silica-magnesia-zirconia, etc. It may also be advantageous to provide at least a part of the foregoing matrix materials in collodial form so as to facilitate extrusion of the bound catalyst component(s).

The relative proportions of finely divided crystalline material and inorganic oxide matrix can vary widely with the zeolite content ranging from about 1 to about 95 percent by weight and more usually, particularly when the composite is prepared in the form of beads, in the range of about 2 to about 80 weight percent of the composite.

The stability of the zeolite catalyst may be increased by steaming, with suitable steam stabilization conditions including contacting the catalyst with, for example, 5-100% steam at a temperature of at least 300° C. (e.g. 300°-650° C.) for at least one hour (e.g. 1-200 hours) at a pressure of 100-2,500 kPa. In a more particular embodiment, the catalyst can be made to undergo steaming with 75-100% steam at 315°-500° C. and atmospheric pressure for 2-25 hours.

The operating temperature of the alkylation process herein can extend over a fairly broad range, e.g., from about −40° to about 250° C. and is preferably within the range of from about −20° C. to about 100° C. The practical upper operating temperature will often be dictated by the need to avoid an undue occurrence of undesirable side reactions.

The pressures employed in the present process can extend over a considerably wide range, e.g., from subatmospheric to about 5000 psig, preferably from atmospheric to about 1000 psig, with process pressure up to about 500 psig useful.

The amount of zeolite used in the present alkylation process can be varied over relatively wide limits. In general, the amount of zeolite as measured by the weight hourly space velocity (WHSV) of the olefin can range from about 0.01 to about 100 $hr^{-1}$, preferably from 0.1 to 20 $hr^{-1}$. It will, of course, be realized by those skilled in the art that the amount of catalyst selected for a particular reaction will be determined by several variables including the reactants involved as well as the nature of the catalyst and the operating conditions employed.

The isoparaffin reactant used in the present alkylation process is one possessing up to about 20 carbon atoms and preferably one having from about 4 to about 8 carbon atoms as, for example, isobutane, 3-methylhexane, 2-methylbutane, 2,3-dimethylbutane and 2,4-dimethylhexane.

The olefin reactant employed herein generally contains from 2 to about 12 carbon atoms. Representative examples are ethylene, propylene, butene-1, butene-2, isobutylene, pentenes, hexenes, heptenes and octenes. Particularly preferred are $C_3$ and $C_4$ olefins and mixtures thereof.

In general, the mole ratio of total isoparaffin to total olefin alkylating agent in the combined hydrocarbon feed can be from about 0.5:1 to about 500:1, such as, for example, from about 0.5:1 to about 100:1, preferably from about 1:1 to about 50:1 and most usually from about 2:1 to about 20:1. The isoparaffin and/or olefin reactants can be in either the vapor phase or the liquid phase and can be neat, i.e., free from intentional admixture of dilution with other material, or the reactants can be brought into contact with the catalyst composition with the aid of carrier gases or diluents such as, for example, hydrogen or nitrogen. The reactants can be combined all at once or incrementally; thus, the process of the invention contemplates multiple introduction of olefins into one or more alkylation reaction zones.

As in the alkylation process of copending U.S. patent application Ser. No. 219,130, filed Jul. 15, 1988, it can be advantageous to add water to the alkylation reactor, e.g., at a rate of from about 0.1 ppmw to about 1 wt %, based upon total hydrocarbon feed rate, preferably at a rate of from about 0.1 ppmw to about 500 ppmw. The water can be supplied as such or as a feed material which produces water under the alkylation conditions selected. Suitable water-producing materials which can be introduced into the reactor without interfering with the desired alkylation include monohydric and dihydric alcohols which yield water upon undergoing dehydration. Of this group, particular preference is accorded the aliphatic alcohols, especially those containing 1 to 6 carbon atoms as, for example, methanol, ethanol, isopropanol, t-butyl alcohol and isopentyl alcohol. The optional water and/or water-producing material can be added directly to the reactor, e.g., with the feed, and/or it can be incorporated into the zeolite catalyst component, either by direct contact therewith or by exposing the zeolite to an atmosphere of water and/or water-producing material. For example, when the added water and/or water-producing material is pre-introduced into the zeolite catalyst component, the amount of water and/or water-producing material taken up by the zeolite can be made to vary from about 0.5 to about 25, and preferably from about 1 to about 10, weight percent of the catalyst.

The alkylation process of the present invention can be carried out as a batch-type, semi-continuous or continuous operation utilizing a fixed or moving bed of the zeolite catalyst component saturated with the Lewis acid component. A preferred embodiment entails use of a catalyst zone wherein the hydrocarbon charge is passed concurrently or countercurrently through a moving bed of particle-form catalyst. The latter, after use, is conducted to a regeneration zone where coke is removed, e.g., by burning in an oxygen-containing atmosphere (such as air) at elevated temperature or by extracting with a solvent, after which the regenerated catalyst is recycled to the conversion zone for further contact with the organic reactants.

A suitable system for carrying out the alkylation process of this invention on a continuous basis is shown in FIG. 1. As shown in the drawing, a stream containing isobutane and propylene and/or butenes along with some normal butane is introduced through line 1 into stirred reactor 3 containing catalyst. Optionally, water and/or a water-producing material such as methanol is introduced through line 2 into the reactor. $BF_3$ is introduced as needed from holding tank 5 through line 6 into the reactor. The amount of $BF_3$ introduced is such as to exceed that which is required to saturate the zeolite catalyst (as well as any binder or matrix material with which the zeolite might be composited). Zeolite catalyst slurry is removed from the reactor and is introduced to settling vessel 4, the recovered zeolite catalyst thereafter being recycled to the alkylation reactor via line 9. The hydrocarbon product mixture is removed from the settling vessel through line 10 and introduced into $BF_3$ stripper 11 from which $BF_3$ is removed as overhead through line 12 and recycled through line 13 to $BF_3$ holding tank 5. The remaining hydrocarbon product mixture is withdrawn from the $BF_3$ stripper through line 14. A portion of such hydrocarbon product mixture is introduced via lines 15 and 16 to fractionator 17. Unreacted isobutane is removed as overhead through line 18 and recycled through line 19 to the reactant feed stream line 1. Desired $C_5+$ alkylate product is withdrawn from the bottom of fractionator 17 through line 20. Any normal butane may be withdrawn from the fractionator through line 21. The remaining portion of the hydrocarbon product mixture passing through line 14 from $BF_3$ stripper 11 is conducted through line 22 to depropanizer 23 from which propane and lighter products are removed as overhead through line 24. Heavier components are removed as bottoms through line 25 and recycled via lines 26 and 16 to fractionator 17. Isobutane is removed from depropanizer 23 through line 27 and recycled through lines 28 and 19 to the initial reactant feed line 1.

In order to more fully illustrate the alkylation process of this invention and the manner of practicing same, the following examples are presented. In examples illustrative of the synthesis of zeolite, whenever sorption data are set forth for comparison of sorptive capacities for water, cyclohexane and/or n-hexane, they were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr of cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. Zeolite MCM-22 always exhibits Equilibrium Adsorption values of greater than about 10 wt. % for water vapor, greater than about 4.5 wt. %, usually greater than about 7 wt. % for cyclohexane vapor and greater than about 10 wt. % for n-hexane vapor. These vapor sorption capacities are a notable distinguishing feature of zeolite MCM-22 and are preferred for the zeolite component of catalyst for use herein.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). It is based on the activity of the highly active silica-alumina cracking catalyst taken as an Alpha of 1 (Rate Constant=0.016 sec $^{-1}$). The Alpha Test is described in U.S. Pat. No. 3,354,078, in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

EXAMPLE 1

One part of sodium aluminate (43.5% $Al_2O_3$, 32.2% $Na_2O$, 25.6% $H_2O$) was dissolved in a solution containing 1 part of 50% NaOH solution and 103.13 parts $H_2O$. To this was added 4.50 parts hexamethyleneimine. The resulting solution was added to 8.55 parts of Ultrasil, a precipitated, spray-dried silica (about 90% $SiO_2$).

The reaction mixture had the following composition, in mole ratios:

| | |
|---|---|
| $SiO_2/Al_2O_3$ = | 30.0 |
| $OH^-/SiO_2$ = | 0.18 |
| $H_2O/SiO_2$ = | 44.9 |
| $Na/SiO_2$ = | 0.18 |
| $R/SiO_2$ = | 0.35 | where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table E. The sorption capacities of the calcined material were measured to be:

| | |
|---|---|
| $H_2O$ | 15.2 wt. % |
| Cyclohexane | 14.6 wt. % |
| n-Hexane | 16.7 wt. % |

The surface area of the zeolite was measured to be 494 $m^2/g$.

The chemical composition of the uncalined material was determined to be as follows:

| Component | wt. % |
|---|---|
| $SiO_2$ | 66.9 |
| $Al_2O_3$ | 5.40 |
| Na | 0.03 |
| N | 2.27 |
| Ash | 76.3 |
| $SiO_2/Al_2O_3$, mole ratio | 21.1 |

TABLE E

| Degrees 2-Theta | Interplanar d-Spacing (A) | $I/I_o$ |
| --- | --- | --- |
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test and was found to have an Alpha Value of 224.

EXAMPLES 3–5

Three separate synthesis reaction mixtures were prepared with compositions indicated in Table F. The mixtures were prepared with sodium aluminate, sodium hydroxide, Ultrasil, hexamethyleneimine (R) and water. The mixtures were maintained at 150° C., 143° C. and 150° C., respectively, for 7, 8 and 6 days respectively in stainless steel autoclaves at autogenous pressure. Solids were separated from any unreacted components by filtration and then water washed, followed by drying at 120° C. The product crystals were subjected to X-ray diffraction, sorption, surface area and chemical analyses. The results of the sorption, surface area and chemical analyses are presented in Table F. The sorption and surface area measurements were of the calcined product.

TABLE F

| Example | 3 | 4 | 5 |
| --- | --- | --- | --- |
| Synthesis Mixture, mole ratios | | | |
| $SiO_2/Al_2O_3$ | 30.0 | 30.0 | 30.0 |
| $OH^-/SiO_2$ | 0.18 | 0.18 | 0.18 |
| $H_2O/SiO_2$ | 19.4 | 19.4 | 44.9 |
| $Na/SiO_2$ | 0.18 | 0.18 | 0.18 |
| $R/SiO_2$ | 0.35 | 0.35 | 0.35 |
| Product Composition, Wt. % | | | |
| $SiO_2$ | 64.3 | 68.5 | 74.5 |
| $Al_2O_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| $SiO_2/Al_2O_3$, mole ratio | 22.5 | 20.9 | 26.0 |
| Adsorption, Wt. % | | | |
| $H_2O$ | 14.9 | 13.6 | 14.6 |
| Cyclohexane | 12.5 | 12.2 | 13.6 |
| n-Hexane | 14.6 | 16.2 | 19.0 |

TABLE F-continued

| Example | 3 | 4 | 5 |
| --- | --- | --- | --- |
| Surface Area, $m^2/g$ | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and 187, respectively.

EXAMPLE 7

To demonstrate a further preparation of the present zeolite 4.49 parts of hexamethyleneimine was added to a solution containing 1 part of sodium aluminate, 1 part of 50% NaOH solution and 44.19 parts of $H_2O$. To the combined solution was added 8.54 parts of Ultrasil silica. The mixture was crystallized with agitation at 145° C. for 59 hours and the resultant product was water washed and dried at 120° C.

Product chemical composition, surface area and adsorption analyses results were as set forth in Table G:

TABLE G

| Product Composition uncalcined | |
| --- | --- |
| C | 12.1 wt. % |
| N | 1.98 wt. % |
| Na | 640 ppm |
| $Al_2O_3$ | 5.0 wt. % |
| $SiO_2$ | 74.9 wt. % |
| $SiO_2/Al_2O_3$, mole ratio | 25.4 |
| Adsorption, wt. % | |
| Cyclohexane | 9.1 |
| N-Hexane | 14.9 |
| $H_2O$ | 16.8 |
| Surface Area, $m^2/g$ | 479 |

EXAMPLE 8

Twenty-five grams of solid crystal product from Example 7 were calcined in a flowing nitrogen atmospheres at 538° C. for 5 hours, followed by purging with 5% oxygen gas (balance $N_2$) for another 16 hours at 538° C.

Individual 3 g samples of the calcined material were ion-exchanged with 100 ml of 0.1N TEABr, TPABr and $LaCl_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| | Exchange Ions | | |
| --- | --- | --- | --- |
| Ionic Composition, wt. % | TEA | TPA | La |
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the zeolite had very good stability under severe hydrothermal treatment.

EXAMPLE 11

This example illustrates the preparation of the present zeolite where X in the general formula, supra, is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:

| | |
|---|---|
| $SiO_2/B_2O_3 =$ | 6.1 |
| $OH^-/SiO_2 =$ | 0.06 |
| $H_2O/SiO_2 =$ | 19.0 |
| $K/SiO_2 =$ | 0.06 |
| $R/SiO_2 =$ | 0.30 | where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 540° C. and found to have the following sorption capacities:

| | |
|---|---|
| $H_2O$ | 11.7 wt. % |
| Cyclohexane | 7.5 wt. % |
| n-Hexane | 11.4 wt. % |

The surface area of the calcined crystalline material was measured (BET) to be 405 $m^2/g$.

The chemical composition of the uncalcined material was determined to be as follows:

| | |
|---|---|
| N | 1.94 wt. % |
| Na | 175 ppm |
| K | 0.60 wt. % |
| Boron | 1.04 wt. % |
| $Al_2O_3$ | 920 ppm |
| $SiO_2$ | 75.9 wt. % |
| Ash | 74.11 wt. % |
| $SiO_2/Al_2O_3$, molar ratio | 1406 |
| $SiO_2/(Al + B)_2O_3$, molar ratio | 25.8 |

EXAMPLE 12

A portion of the calcined crystalline product of Example 11 was treated with $NH_4Cl$ and again calcined. The final crystalline product was tested in the Alpha test and found to have an Alpha Value of 1.

EXAMPLE 13

This example illustrates another preparation of the zeolite in which X of the general formula, supra, is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:

| | |
|---|---|
| $SiO_2/B_2O_3 =$ | 12.3 |
| $OH^-/SiO_2 =$ | 0.056 |
| $H_2O/SiO_2 =$ | 18.6 |
| $K/SiO_2 =$ | 0.056 |
| $R/SiO_2 =$ | 0.30 | where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

| | |
|---|---|
| $H_2O$ | 14.4 wt. % |
| Cyclohexane | 4.6 wt. % |
| n-Hexane | 14.0 wt. % |

The surface area of the calcined crystalline material was measured to be 438 $m^2/g$.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio | 249 |
| $SiO_2/(Al + B)_2O_3$, molar ratio | 28.2 |

EXAMPLE 14

A portion of the calcined crystalline product of Example 13 was tested in the Alpha Test and found to have an Alpha Value of 5.

EXAMPLE 15

This example compares the alkylation performance of a $BF_3$-promoted MCM-22 zeolite alkylation catalyst composition in accordance with this invention and a $BF_3$-promoted silica alkylation catalyst composition.

The MCM-22 catalyst used in this example was prepared by adding 4.49 parts quantity of hexamethyleneimine to a mixture containing 1.00 part sodium aluminate, 1.00 part 50% NaOH, 8.54 parts Ultrasil VN3 and 44.19 parts deionized $H_2O$. The reaction mixture was heated to 143° C. (290° F.) and stirred in an autoclave at that temperature for crystallization. After full crystallinity was achieved, the majority of the hexamethyleneimine was removed from the autoclave by controlled distillation and the zeolite crystals separated from the remaining liquid by filtration, washed with deionized $H_2O$ and dried. The zeolite was activated by calcining in $N_2$ at 1000° F. for six hours, followed by aqueous ammonium nitrate exchange and calcining in air at 1000° F. for six hours.

In separate runs, 10 g of each of the foregoing catalyst compositions and 300 ml isobutane were charged to a reactor. Following cooling of the reactor contents to the desired alkylation temperature accompanied by constant stirring at 1900 rpm, $BF_3$ gas was introduced to the reactor at a flow rate of 3 wt. % of the total hydrocarbon feed. The feed olefin was then continuously introduced into the reactor to initiate alkylation. The mole ratio of isobutanes to total olefin was 10:1, the reaction temperatures were 0° or 20° C. as indicated below, and the WHSV (based on total olefin) was 1.3 hr$^{-1}$. The composition of the feed is given in Table H and results of the alkylation operations for both catalyst compositions are set forth in Table I as follows:

TABLE H

| Composition of Paraffin-Olefin Feed | |
|---|---|
| Feed Component | Wt. % |
| propylene | 3.30 |
| isobutylene | 1.24 |
| 1-butene | 1.01 |
| 2-butene | 2.14 |
| isobutane | 92.31 |

TABLE I

Comparison of Lewis Acid Promoted Silica and Lewis Acid Promoted Zeolite MCM-22

| | BF$_3$-Promoted SiO$_2$ | | BR$_3$-Promoted MCM-22 | |
|---|---|---|---|---|
| Alkylation Temp., °C. | 0 | 20 | 0 | 20 |
| C$_5$+ Product, wt. % | | | | |
| C$_5$ | 2.9 | 7.2 | 2.5 | 5.4 |
| C$_6$ | 3.4 | 6.9 | 3.1 | 5.4 |
| C$_7$ | 36.2 | 31.2 | 39.4 | 34.6 |
| C$_8$ | 49.9 | 39.3 | 50.4 | 47.1 |
| C$_9$+ | 7.6 | 15.4 | 4.6 | 7.4 |
| IMP/DMH* | 2.0 | 1.4 | 2.2 | 1.6 |
| Octane, Raw Gasoline | | | | |
| RON + 0 | 93.9 | 90.7 | 95.5 | 91.5 |
| MON + 0 | 92.2 | 89.3 | 92.2 | 89.6 |

*TMP = trimethylpentanes
DMH = dimethylhexanes

EXAMPLE 16

Example 15 was substantially repeated but with a feed having the composition set forth in Table J as follows:

TABLE J

| Composition of Paraffin-Olefin Feed | |
|---|---|
| Olefin | Propylene + Butenes |
| Isobutane:Olefin Mole Ratio | 5.7:1 |
| Feed Component | Wt. % |
| propylene | 5.60 |
| isobutylene | 2.90 |
| 1-butene | 2.00 |
| 2-butene | 4.45 |
| isobutane | 84.40 |
| n-butane | 0.65 |

The results of the alkylation operations are set forth in Table K as follows:

TABLE K

Comparison of Lewis Acid Promoted Silica and Lewis Acid Promoted Zeolite MCM-22

| | BF$_3$-Promoted SiO$_2$ | | BF$_3$-Promoted MCM-22 | |
|---|---|---|---|---|
| Alkylation Temp., °C. | 0 | 20 | 0 | 20 |
| C$_5$+ Product, wt. % | | | | |
| C$_5$ | 2.5 | 4.0 | 3.0 | 3.7 |
| C$_6$ | 2.6 | 3.5 | 3.3 | 3.4 |
| C$_7$ | 28.6 | 22.9 | 2.5 | 20.4 |
| C$_8$ | 56.8 | 56.0 | 64.7 | 63.9 |
| C$_9$+ | 9.4 | 13.6 | 6.4 | 8.6 |
| TMP/DMH | 2.2 | 1.6 | 2.2 | 1.6 |
| Octane, Raw Gasoline | | | | |
| RON + 0 | 93.2 | 86.8 | 93.5 | 88.4 |

TABLE K-continued

Comparison of Lewis Acid Promoted Silica and Lewis Acid Promoted Zeolite MCM-22

| | BF$_3$-Promoted SiO$_2$ | | BF$_3$-Promoted MCM-22 | |
|---|---|---|---|---|
| Alkylation Temp., °C. | 0 | 20 | 0 | 20 |
| MON + 0 | 92.1 | 88.3 | 92.0 | 88.2 |

EXAMPLE 17

Example 15 was substantially repeated but with a feed having the composition set forth in Table L as follows:

TABLE L

| Composition of Paraffin-Olefin Feed | |
|---|---|
| Olefin | Propylene + Butenes |
| Isobutane:Olefin Mole Ratio | 10:1 |
| Feed Component | Wt. % |
| isobutylene | 5.73 |
| 1-butene | 0.26 |
| 2-butene | 2.98 |
| isobutane | 90.93 |
| n-butane | 0.10 |

The results of the alkylation operations are set forth in Table M as follows:

TABLE M

Comparison of Lewis Acid Promoted Silica and Lewis Acid Promoted Zeolite MCM-22

| | BF$_3$-Promoted SiO$_2$ | | BF$_3$-Promoted MCM-22 | |
|---|---|---|---|---|
| Alkylation Temp., °C. | 0 | 20 | 0 | 20 |
| C$_5$+ Product, wt. % | | | | |
| C$_5$ | 4.9 | 7.0 | 4.3 | 6.4 |
| C$_6$ | 4.5 | 4.7 | 3.4 | 4.5 |
| C$_7$ | 4.1 | 5.3 | 3.4 | 4.9 |
| C$_8$ | 77.9 | 71.9 | 83.5 | 77.7 |
| C$_9$+ | 8.7 | 11.2 | 5.5 | 6.6 |
| TMP/DMH | 5.1 | 2.9 | 4.9 | 2.9 |
| Octane, Raw Gasoline | | | | |
| RON + 0 | 95.5 | 92.8 | 95.9 | 93.1 |
| MON + 0 | 93.1 | 91.7 | 94.2 | 93.1 |

EXAMPLE 18

Example 15 was substantially repeated but with a feed having the composition set forth in Table N as follows:

TABLE N

| Composition of Paraffin-Olefin Feed | |
|---|---|
| Oelfin | Propylene + Butenes |
| Isobutane:Olefin Mole Ratio | 12.9:1 |
| Feed Component | Wt. % |
| propylene | 3.22 |
| isobutylene | 2.74 |
| 1-butene | 0.15 |
| 2-butene | 1.24 |
| isobutane | 92.50 |
| n-butane | 0.15 |

The results of the alkylation operation are set forth in Table O as follows:

TABLE O

Comparison of Lewis Acid Promoted Silica and Lewis Acid Promoted Zeolite MCM-22

| | BF$_3$-Promoted SiO$_2$ | | BF$_3$-Promoted MCM-22 | |
|---|---|---|---|---|
| Alkylation Temp., °C. | 0 | 20 | 0 | 20 |
| C$_5$+ Product, wt. % | | | | |
| C$_5$ | 6.5 | 10.1 | 3.3 | 4.9 |
| C$_6$ | 6.3 | 8.8 | 3.0 | 4.3 |
| C$_7$ | 38.6 | 32.7 | 37.8 | 25.6 |
| C$_8$ | 33.7 | 29.7 | 51.4 | 59.4 |
| C$_9$+ | 14.8 | 18.7 | 4.6 | 5.9 |
| TMP/DMH | 4.1 | 2.1 | 5.4 | 3.0 |
| Octane, Raw Gasoline | | | | |
| RON + 0 | 92.9 | 90.5 | 93.2 | 93.3 |
| MON + 0 | 90.7 | 89.5 | 92.8 | 91.7 |

EXAMPLE 19

Example 15 was substantially repeated but with a feed having the composition set forth in Table P as follows:

TABLE P

Composition of Paraffin-Olefin Feed

| Olefin | Butene |
|---|---|
| Isobutane:Olefin Mole Ratio | 9.6:1 |
| Feed Component | Wt. % |
| 2-butene | 9.4 |
| isobutane | 90.60 |

The results of the alkylation operation are set forth in Table Q as follows:

TABLE Q

Comparison of Lewis Acid Promoted Silica and Lewis Acid Promoted Zeolite MCM-22

| | BF3-Promoted SiO$_2$ | | BF$_3$-Promoted MCM-22 | |
|---|---|---|---|---|
| Alkylation Temp., °C. | 0 | 20 | 0 | 20 |
| C$_5$+ Product, wt. % | | | | |
| C$_5$ | 2.7 | 7.1 | 1.9 | 3.6 |
| C$_6$ | 2.7 | 5.6 | 2.0 | 3.2 |
| C$_7$ | 2.8 | 6.3 | 1.9 | 3.9 |
| C$_8$ | 82.9 | 63.9 | 92.2 | 86.8 |
| C$_9$+ | 8.9 | 17.2 | 2.0 | 2.6 |
| TMP/DMH | 5.9 | 2.8 | 6.7 | 3.4 |
| Octane, Raw Gasoline | | | | |
| RON + 0 | 97.3 | 93.2 | 98.2 | 94.8 |
| MON + 0 | 94.0 | 91.9 | 95.6 | 93.3 |

What is claimed is:

1. An isoparaffin-olefin alkylation process which comprises reacting isoparaffin and olefin under alkylation conditions in the presence of a Lewis acid-promoted catalyst to provide an alkylate product, wherein said catalyst comprises a zeolite characterized by an X-ray diffraction pattern including interplanar d-spacings as set forth in Table A of the specification.

2. The process of claim 1, wherein the zeolite is characterized by an X-ray diffraction pattern including interplanar d-spacings as set forth in Table B of the specification.

3. The process of claim 1, wherein the zeolite is characterized by an X-ray diffraction pattern including interplanar d-spacings as set forth in Table C of the specification.

4. The process of claim 1, wherein the zeolite is characterized by an X-ray diffraction pattern including interplanar d-spacings as set forth in Table D of the specification.

5. The process of claim 1, wherein the zeolite has a composition comprising the molar relationship $$X_2O_3:(n)YO_2,$$

wherein n is at least about 10, X is a trivalent element and Y is a tetravalent element.

6. The process of claim 1 wherein the zeolite possesses equilibrium adsorption capacities of greater than about 4.5 wt. % for cyclohexane vapor and greater than about 10 wt. % for n-hexane vapor.

7. The process of claim 5, wherein X is selected from the group consisting of aluminum, boron, iron, gallium and combinations thereof and Y is selected from the group consisting of silicon, germanium and combinations thereof.

8. The process of claim 5, wherein X comprises aluminum and Y comprises silicon.

9. The process of claim 1, wherein the zeolite has been thermally treated at a temperature up to about 925° C. in the presence or absence of steam.

10. The process of claim 1, wherein the isoparaffin contains from 4 to 8 carbon atoms and the olefin contains from 2 to 12 carbon atoms.

11. The process of claim 1, wherein the Lewis acid is selected from the group consisting of BF$_3$, BCl$_3$, SbF$_3$ and AlCl$_3$.

12. The process of claim 1, wherein the alkylation is carried out in the presence of water and/or other material which produces water under alkylation reaction conditions.

13. The process of claim 1, wherein the reaction is carried out under sufficient pressure to maintain at least one of the reactants in the liquid phase.

14. The process of claim 1, wherein the mole ratio of total isoparaffin to total olefin is from about 0.5:1 to about 500:1.

15. The process of claim 14, wherein the mole ratio of total isoparaffin to total olefin is from about 1:1 to about 50:1.

16. The process of claim 1, wherein the isoparaffin is isobutane and the olefin is propylene and/or butene(s).

17. The process of claim 12, wherein the water and/or water-producing material is pre-introduced into the zeolite.

18. The process of claim 12, wherein the water and/or water-producing material is co-fed with the reactants.

19. The process of claim 12, wherein the amount of water ranges from about 0.1 ppmw to about 1 weight percent based upon the total hydrocarbon feed rate.

20. The process of claim 19, wherein the amount of water ranges from about 0.1 ppmw to about 500 ppmw based upon the total hydrocarbon feed rate.

21. The process of claim 1, wherein the alkylation reaction temperature is from about −40° C. to about 250° C. and the weight hourly space velocity of the olefin is from about 0.01 hr $^{-1}$ to 100 hr $^{-1}$.

22. The process of claim 1, wherein the alkylation reaction temperature is from about −20° C. to about 100° C. and the weight hourly space velocity of the olefin is from about 0.1 hr $^{-1}$ to about 20 hr $^{-1}$.

23. The process of claim 1 wherein said zeolite is composited with a matrix material.

24. The process of claim 23, wherein said matrix material is selected from the group consisting of silica, alumina, zirconia, titania, beryllia, magnesia, thoria, and combinations thereof.

* * * * *